United States Patent [19]

Atlee, III

[11] Patent Number: 5,329,922
[45] Date of Patent: Jul. 19, 1994

[54] OXIMETRIC ESOPHAGEAL PROBE

[76] Inventor: John L. Atlee, III, N71 W29436 Tamron La., Hartland, Wis. 53029

[21] Appl. No.: 963,072

[22] Filed: Oct. 19, 1992

[51] Int. Cl.⁵ .............................................. A61B 5/00
[52] U.S. Cl. ...................................... 128/632; 128/634
[58] Field of Search ................................ 128/632-635; 356/41

[56] References Cited

U.S. PATENT DOCUMENTS

| | | | |
|---|---|---|---|
| 3,690,769 | 9/1972 | Mori | 356/41 |
| 3,847,483 | 11/1974 | Shaw et al. | 356/41 |
| 3,912,614 | 10/1975 | Spracklen et al. | 128/635 |
| 3,951,136 | 4/1976 | Wall | |
| 4,090,518 | 5/1978 | Elam | |
| 4,114,604 | 9/1978 | Shaw et al. | |
| 4,176,660 | 12/1979 | Mylrea et al. | 128/671 |
| 4,475,555 | 10/1984 | Linder | 128/670 |
| 4,476,872 | 10/1984 | Perlin | 128/642 |
| 4,623,248 | 11/1986 | Sperinde | 356/41 |
| 4,640,298 | 2/1987 | Pless et al. | |
| 4,672,971 | 6/1987 | Otten | 128/635 |
| 4,697,593 | 10/1987 | Evans et al. | 356/41 X |
| 4,714,080 | 12/1987 | Edgar, Jr. et al. | 128/633 |
| 4,796,636 | 1/1989 | Branstetter et al. | 128/633 |
| 4,807,630 | 2/1989 | Malinouskas | 356/41 X |
| 4,880,304 | 11/1989 | Jaeb et al. | 356/41 |
| 5,005,573 | 4/1991 | Buchanan | 128/633 X |
| 5,193,544 | 3/1993 | Jaffe | 128/634 |
| 5,205,281 | 4/1993 | Buchanan | 128/633 X |

OTHER PUBLICATIONS

Christine Z. Pattison, M.D., et al., "Atrial Pacing Thresholds Measured in Anesthetized Patients with the Use of an Esophageal Stethoscope Modified for Pacing", Anesthesiology, vol. 74, No. 5, May, 1991, pp. 854-859.

Primary Examiner—Lee S. Cohen
Assistant Examiner—Samuel Gilbert
Attorney, Agent, or Firm—Michael, Best & Friedrich

[57] ABSTRACT

An esophageal probe comprising an elongated tubular body member with a distal portion that is insertible into an esophagus and a pair of oximeter sensors mounted in a spaced apart relation on the body for generating electrical signals functionally related to the fraction of hemoglobin in blood in the form of oxyhemoglobin.

11 Claims, 1 Drawing Sheet

OXIMETRIC ESOPHAGEAL PROBE

BACKGROUND OF THE INVENTION

The invention relates to a method and apparatus for measuring the oxygen concentration in blood. More particularly, the invention relates an esophageal probe having an oximeter sensor for measuring the fraction of hemoglobin (HGB) that is present in the form of oxyhemoglobin (HGBO) and a method of positioning the oximeter sensor in the esophagus.

Oximetry is the measurement of the fraction of hemoglobin (HGB) that is present in the form of oxyhemoglobin (HGBO). When oxygen is taken into the lungs, it is transferred across the alveolar membrane to the blood cells and chemically attaches to hemoglobin molecules (HGB) to form oxyhemoglobin (HGBO). Therefore, the amount of oxygen being transferred from the lungs into the blood stream can be deduced by measuring the fraction of HGB that is present in the form of HGBO. It is important to know the oxygen levels in order to determine the efficacy of cardiac function and perfusion (i.e., delivery of oxygen to tissue).

One method of making this measurement involves a technique called surface oximetry. A finger or earlobe is placed between, on the one side, a pair of light emitting diodes and, on the other side, a pair of photo-transistors. Light having two separate wavelengths is directed through the tissue and is detected by the photo-transistors on the opposite side. By comparing the ratios of the light absorbed by the tissue at each wavelength, the fraction of HGB in the form of HGBO can be determined.

However, surface oximetry is quite often unreliable or ineffective in hypothermic or peripherally vaso-constricted patients. Vaso-constriction is a common symptom of shock. Consequently, oximetry has been provided as a feature of some models of pulmonary artery catheters. Systemic arterial oximetry has been reported or is available as well. Systemic or pulmonary arterial oximetry readings are often more reliable than those obtained by surface oximetry since measurements are directly from the blood itself. Unfortunately, arterial oximetry by its very nature, requires a much greater degree of medical invasiveness and a corresponding degree of risk to the patient.

Since the esophagus is a core body organ and presumably well-perfused except under the most extreme circumstances, it has been determined that the esophagus could be an ideal locus for pulse oximetry measurements. This is especially so for anesthesiologists and critical care physicians who intubate the esophagus more or less routinely to monitor heart and breath sounds as well as core body temperature. Additionally, they frequently manage patients with hypothermia or in shock. Thus, it is desirable to provide an esophageal probe having a pulse oximeter therein for monitoring oxygen delivery to the esophageal mucosal tissue.

It has further been determined that for an oximetric sensor to make accurate measurements in the esophagus, it must be located somewhere in the middle third, the upper third, or even the upper three-fourths of the esophagus as measured from the gastro-esophageal junction to the hypo-pharynx. This is because the circulation to and from the esophagus at the area comprising the lower third or lower quarter of the esophagus is, in part, portal venous flow and hepatic venous flow or systemic venous flow and portal venous flow. In either case, because the flow is a mixture of portal and venous blood, it has a higher oxygen tension and therefore oximetric readings from the lower third or lower quarter of the esophagus would not provide a representative picture of cardiac function or perfusion to other body tissues.

Thus, it is desirable to provide an esophageal probe to monitor heart sounds, breath sounds, and body temperature which could include a pulse oximeter for measuring the fraction of HGB in the form of HGBO.

It is further desirable to provide an esophageal probe that can operate to locate the pulse oximeter in the upper two thirds or three fourths of the esophagus and still provide the various other functions for which it is intended.

SUMMARY OF THE INVENTION

According to one aspect, the invention comprises an esophageal probe comprising an elongated tubular hollow body member having a distal portion that is insertible into an esophagus and at least one oximeter sensor carried by the body.

According to another aspect, the invention comprises a method for measuring the fraction of hemoglobin in blood in the form of oxyhemoglobin. The method involves inserting an esophageal probe-mounted oximeter into the esophagus of an animal organism, generating signals functionally related to the oxyhemoglobin concentration in the blood within the esophageal tissue of the animal organism and determining the oxyhemoglobin concentration from the signals.

It is an object of the invention to provide a new and improved esophageal probe for use in measuring the oxygen concentration in blood.

It is a further object of the invention to provide an esophageal probe that includes an oximeter sensor for measuring the fraction of HGB present in the blood in the form of HGBO.

It is another object of the invention to provide an esophageal probe which may be used to determined the efficiency of cardiac function and tissue perfusion.

It is a further object to provide an esophageal probe capable of providing more reliable oximetry measurements from patients suffering from hypothermia or shock.

A still further object is to provide an esophageal probe and method for making oximetric measurements from the upper two-thirds to three fourths of the esophagus as measured from the gastro-esophageal junction to the hypo-pharynx.

DETAILED DESCRIPTION OF THE PREFERRED EMBODIMENT

Figure 1:
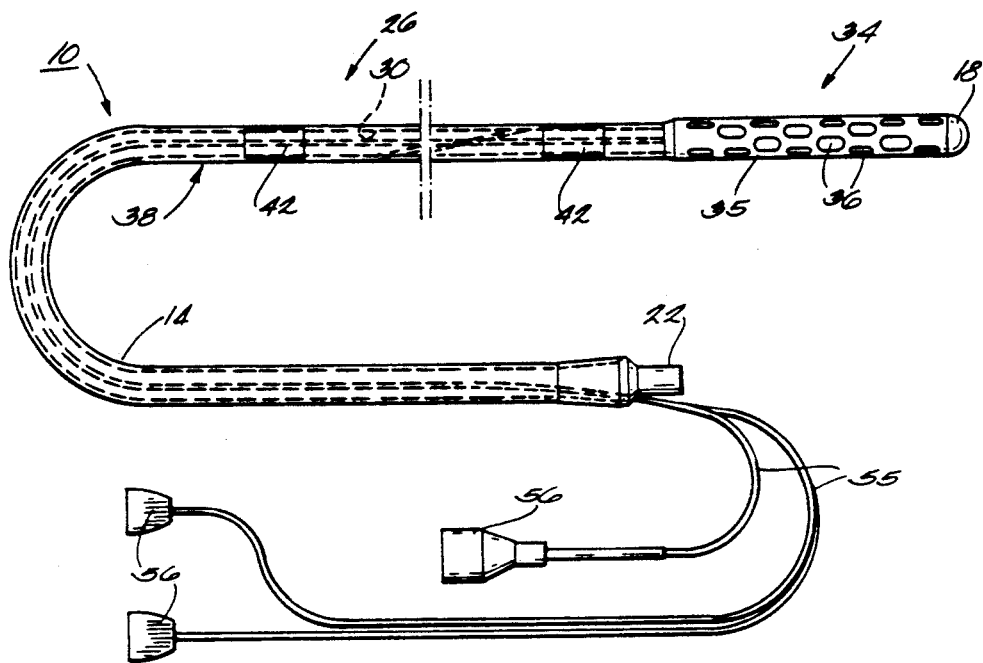
FIG. 1 of the drawings is a side elevational view of an esophageal probe and a pair of oximeter sensors mounted therein.

FIG. 1 illustrates an esophageal probe 10 according to the preferred embodiment of the invention. The esophageal probe 10 includes an elongated tubular hollow body member 14 having a distal end 18 for insertion into an esophagus and a proximal end 22 designed to extend out of the esophagus and mouth of the patient when the probe 10 is in use. The body member 14 defines a contact portion 26 for contact with the esophagus and a lumen 30 extending along the length of the probe and exiting through the proximal end 22. The contact portion 26 has a distal end 34 which is designed to communicate with the esophageal gastric junction and a proximal end 38 designed to communicate with the hypo-pharynx. An acoustic diaphragm 35 overlying perforations 36 may be disposed in the distal end 34 of body member 14 for listening to heart and breath sounds.

The esophageal probe 10 also includes at least one oximeter sensor 42 carried by the body member 14. While the oximetry sensor 42 may be positioned anywhere along the portion 26 that is in contact with the esophageal mucosa, in the preferred form of the invention, the oximeter sensor 42 is disposed in the upper or proximal two-thirds to three-fourths of the contact portion 26. A pair of oximeter sensors 42 are shown in FIG. 1 to illustrate that it may be desirable to provide multiple oxygen sensors on the probe. For example, it may be desirable to measure the oxygen saturation (OS) at two or more levels in the esophagus such as at the distal one-third of the esophagus and at the proximal one-third. This provides a differential determination of delivery and utilization of oxygen for core body organs at different levels in the body. Alternatively, it may be desirable to combine surface, peripheral, or pulmonary oximetry with esophageal oximetry to make diagnoses concerning the adequacy of tissue oxygen delivery and utilization.

The oximeter sensor 42 provides a means for generating electrical signals which may be employed in the determination of the level of oxygen saturation in the blood. The preferred form of the invention employs reflectance pulse oximetry, the operation of which is shown conceptually in FIG. 2. However, other methods of oximetry such as colorimetric or transmittance oximetry may be employed. If colorimetric oximetry is used, special dyes are applied to the esophageal mucosa and the absorption characteristics of the dyed tissue relative to the transmitted light are measured. If transmittance oximetry is employed, light could be transmitted from the esophageal mucosa to an oximeter sensor located external to the body on the neck. The details of these methods of oximetry measurement are well known in the art and form no part of the present invention. However, a brief of description of reflectance oximetry will follow in order to provide some useful background.

The reflectance oximeter is an optical instrument which is used to measure the concentration of oxygen in the blood. Particularly, the oximeter measures the fraction of hemoglobin that is present in the form of oxyhemoglobin. In the case of the reflectance oximeter used in the preferred form of the invention, the instrument measures the blood OS by taking advantage of the differences in the absorption spectra of HGB and HGBO. In short, the oximeter illuminates the patients tissue, and accordingly, the blood coursing through the tissue with light of two different wavelengths. Some of the light is absorbed by the tissue and blood, some of the light is transmitted through the tissue, and some of the light is reflected. An optical sensor measures the reflected light and generates electrical signals which are used to determine the OS in a manner well known in the art.

In the preferred form of the invention, the oximeter sensor 42 has a first emitter 46 such as a light emitting diode (LED) which emits red light having a wavelength of approximately 640 nanometers, and a second emitter 50 which emits an infra-red light having a wavelength of approximately 960 nanometers. In the embodiment shown in FIG. 1, the emitters 46, 50 are located on a common substrate 54 disposed on the hollow body member 14. The substrate 54 may be located in the hollow body member 14 in the region occupying the upper two-thirds to three-fourths of the contact portion of the esophageal probe. Those skilled in the art will appreciate that circuitry, not shown, will be provided to energize the light emitters 46 and 50 alternately so that the level of reflected light at each wavelength can be individually detected.

Figure 2:
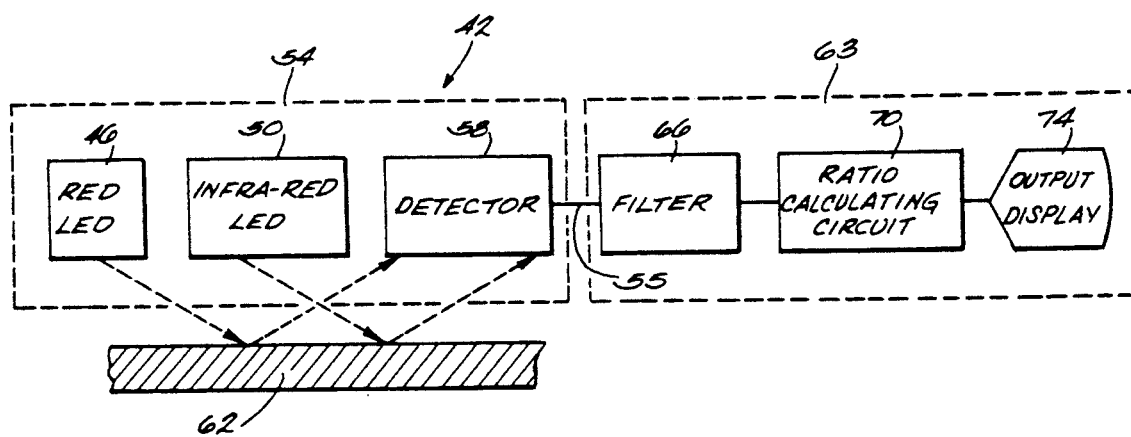
FIG. 2 of the drawings is a conceptual view of the oximeter employed in the probe of the preferred embodiment.

The sensor 42 also includes a detector 58 for sensing the light reflected from the illuminated tissue and blood and for generating electrical signals representing the amount of reflected light measured. The detector 58 is capable of detecting the red light emitted from the first emitter 46 and reflected from the well perfused esophageal tissue 62 (FIG. 2). Likewise, the detector 58 is also capable of detecting the infrared light emitted from the second emitter 50 and reflected from the same esophageal tissue 62. In the preferred form of the invention, the detector is disposed on the substrate 54 along with the emitters 46, 50. However, it may at times be desirable to provide an embodiment having a separate substrate for the emitters 46, 50 and the detector 58. In that event, it would nevertheless be necessary to have the detector 58 proximately disposed to the emitters 46, 50 so as to be able to measure the reflected light with a minimum amount of interference and dissipation.

The oximeter sensor 42 also includes lead wires 55 extending along the length of the hollow body member 14 from the oximeter sensor 42 to the proximal end 22 of the hollow body member. The lead-wires 55 are connected on one end to the detector and emitters 46, 50 of the oximeter sensor 42 and extend from the sensor 42 through the lumen 30 and are terminated by connectors 56 appropriate for connecting the sensor 42 to electronic instrumentation 63 which determines oxygen saturation in a manner well known in the art.

Referring still to FIG. 2, the detector 58 is connected via lead-wires 55 to an electronic filter 66 for filtering the electronic signals generated by the detector 58. The filter 66 in turn is connected to a ratio calculating circuit 70 which utilizes the signals generated by the detector 58 which are indicative of the reflected red and infrared light to calculate the ratio of HGB present in the form of HGBO. Once calculated, the ratio is transmitted to output display 74 for output in a form that is clinically meaningful. If plural oximetry probes are employed, the HGBO determination at each level of the esophagus will be calculated and displayed.

In operation, the esophageal probe 10 is inserted into the esophagus 62 through the mouth, pharynx, and hypo-pharynx of the patient so as to position the contact portion 26 appropriately within the esophagus. In the preferred form of the invention, the probe will be similar to conventional esophageal stethoscopes. Thus, it must be sufficiently rigid to allow insertion into the esophagus, but be sufficiently pliable to prevent damage to the tissue. The materials employed in the probe must bio-compatible and non-biodegradable, and the surfaces must be non-abrasive and relatively soft or pliable so as not to pose the risk of esophageal mucosa abrasion or tear. The tip of the hollow tubular member must also be relatively soft and pliable so as not to cause esophageal perforation.

The oximeter sensor 42 can take the form of any existing commercially available oximeters so long as it is bio-compatible, non-corrosive, and non-biodegradable. Because the probe 10 can be used for other applications and to measure other select biophysical parameters, it is conceived that many different kinds of transducers and thus many different types of materials will be used in the probe. All of these materials must be non-biodegradable for at least a period of several months, since this would otherwise effect the operation of the probe if used for extended periods of up to several days. In the preferred embodiment, the hollow tubular member 14 is formed of polyvinylchloride.

The contact portion 26 is appropriately positioned in the esophagus 62 so that the oximeter sensor 42 is disposed in the upper two-thirds to three-fourths of the portion of the esophagus extending from the gastro-esophageal junction to the hypo-pharynx. This portion of the esophagus is deemed ideal for the oximetry measurement because it provides a representative picture of the true OS. If the measurement were taken in the lower one-third or one-fourth of the esophagus portion, the readings would not be representative of the true OS because the circulation to and from the esophagus at these lower levels is, in part, portal-venous flow and hepatic-venous flow or systemic-venous flow and portal-venous flow. In either case, because the flow is a mixed (partially arterialized) venous flow it has a higher oxygen tension and therefore, the readings would not be representative of true OS of the patient. While the particular region in the esophagus from which a representative OS determination may be obtained will vary from patient to patient, there is some point in the esophagus above which the normal type of venous and arterial blood flow exists. It is this region from which the oximetric measurement should be obtained.

The invention also comprises a method for measuring the fraction of HGB in blood in the form of HGBO. The preferred form of the method embodying the invention includes the steps of inserting an esophageal probe-mounted oximeter sensor 42 into the esophagus 62 of the patient, determining the HGBO concentration in the blood of the patient as a fraction of the total blood HGB, and generating a display or alarm indicative of this determination. The steps of determining and displaying the HGBO concentration are well known in the art and the particular techniques involved form no part of the invention.

One form of the method embodying the invention further includes the steps of positioning the esophageal probe so that a plurality of oximeter sensors 42 are positioned in a spaced apart relation in the upper three-fourths of the esophagus portion extending proximally from the gastro-esophageal junction.

While only a few embodiments have been illustrated and described, the invention is not intended to limited thereby, but only by the scope of the appended claims.

I claim:

1. An esophageal probe comprising:
   an elongated tubular hollow body member having a distal portion that is insertible into an esophagus of a patient and including a probe having a contact portion, having a length for contact with the esophagus, said contact portion having a distal end for communicating with a gastro-esophageal junction of the patient and a proximal end for communicating with a hypo-pharynx of the patient, one third of the length of said contact portion from said distal end defining a distal third and a remaining two thirds defining a proximal two thirds, and an oximeter sensor located in the proximal two thirds of said contact portion, said oximeter sensor being constructed and arranged to measure a level of oxygen saturation in a patient's blood in tissue located in that portion of the esophagus adjacent the proximal two thirds of said contact portion.

2. The esophageal probe as set forth in claim 1 wherein said oximeter sensor comprises means for alternately emitting light energy of selected wavelengths, means for detecting light energy of selected wavelengths, and means for transducing said light energy detected at said selected wavelengths to generate electrical signals functionally related to the level of said oxygen saturation.

3. The esophageal probe as set forth in claim 2 wherein said light energy emitting means comprises a red light emitter capable of emitting light at red wavelengths and an infrared light emitter capable of emitting light at infrared wavelengths.

4. The esophageal probe as set forth in claim 3 wherein said oximeter sensor is a reflective pulse oximeter.

5. An esophageal probe comprising:
   an elongated tubular hollow body member having a distal portion constructed and arranged to be inserted into an esophagus of a patient and including a probe having a contact portion, having a length, for contact with the esophagus, said contact portion having a distal end for communicating with a gastro-esophageal junction of the patient and a proximal end for communicating with a hypo-pharynx of the patient, one quarter of the length of said contact portion from said distal end defining a distal quarter and a remaining three quarters defining a proximal three quarters, and an oximeter sensor located in the proximal three quarters of said contact portion, said oximeter sensor being constructed and arranged to measure a level of oxygen saturation in a patient's blood.

6. An esophageal probe comprising:
   an elongated tubular hollow body member having a distal portion that is insertable into an esophagus of a patient and including a probe having an elongated contact portion, having a length for contact with the patient's esophagus, said contact portion having a distal end for communicating with a gastro-esophageal junction of the patient and a proximal end for communicating with a hypo-pharynx of the patient, and a pair of oximeter sensors mounted in a spaced apart relation on said elongated contact portion.

7. The esophageal probe set forth in claim 6 wherein one third of the length of said contact portion from said distal end defining a first location and two thirds of the length of said contact portion from said distal end defining a second location, one of said pair of oximeter sensors being mounted on said contact portion at each location.

8. A method for measuring a fraction of hemoglobin in blood in a form of oxyhemoglobin, the method comprising:
   inserting an esophageal probe mounted oximeter sensor into an esophagus of a patient;

positioning the oximeter sensor in that portion of the patient's esophagus located in an upper three-fourths thereof as measured proximally from the patient's gastro-esophageal junction;

generating signals functionally related to an oxyhemoglobin concentration in the blood within esophageal tissue of the patient's said upper three fourths portion;

determining the oxyhemoglobin concentration of said blood from said signals.

9. A method for measuring a fraction of hemoglobin in blood in a form of oxyhemoglobin, the method comprising;

inserting an esophageal probe mounted oximeter sensor into an esophagus of a patient;

positioning the oximeter sensor in that portion of the patient's esophagus located in an upper two thirds thereof as measured proximally from the patient's gastro-esophageal junction;

generating signals functionally related to an oxyhemoglobin concentration in the blood within esophageal tissue of the patient at a location within said upper two thirds portion;

determining the oxyhemoglobin concentration of said blood from said signals.

10. The method set forth in claim 9 and including the steps of generating said signals functionally related to the oxyhemoglobin concentration in the blood at plural levels of the esophagus of the patient and determining the oxyhemoglobin concentration at said plural levels from said signals.

11. The method set forth in claim 10 and including the steps of generating said signals functionally related to the oxyhemoglobin concentration in the blood of the patient at levels approximately one third and two thirds of the length of the esophagus measured from the gastro-esophageal junction.

* * * * *